(12) United States Patent
Chang (10) Patent No.: US 8,163,934 B2
(45) Date of Patent: *Apr. 24, 2012

(54) ULTRAVIOLET LIGHT ABSORBING KETONES OF 2-(2-HYDROXYPHENYL) BENZOTRIAZOLE

(76) Inventor: Chia-Hu Chang, Tappan, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/924,940

(22) Filed: Oct. 8, 2010

(65) Prior Publication Data

US 2011/0038816 A1 Feb. 17, 2011

Related U.S. Application Data

(63) Continuation of application No. 12/286,921, filed on Oct. 4, 2008, now Pat. No. 7,847,103.

(51) Int. Cl.
C07D 249/00 (2006.01)
C08G 18/80 (2006.01)
(52) U.S. Cl. ............ 548/255; 524/86; 524/91; 524/104; 524/106
(58) Field of Classification Search .............. 548/255
See application file for complete search history.

(56) References Cited

U.S. PATENT DOCUMENTS

| | | | |
|---|---|---|---|
| 3,004,896 A | 10/1961 | Heller et al. | |
| 3,213,058 A | 10/1965 | Boyle et al. | |
| 3,496,136 A | 2/1970 | Susi et al. | |
| 3,766,205 A | 10/1973 | Heller et at | |
| 3,936,418 A | 2/1976 | Pond et al. | |
| 4,129,521 A | 12/1978 | Stobel | |
| 4,226,763 A | 10/1980 | Dexter et al. | |
| 4,275,004 A | 6/1981 | Winter et al. | |
| 4,278,589 A | 7/1981 | Dexter et al. | |
| 4,314,933 A | 2/1982 | Berner | |
| 4,426,471 A | 1/1984 | Berner | |
| 4,853,471 A | 8/1989 | Rody et al. | |
| 5,032,489 A | 7/1991 | Kobayashi et al. | |
| 5,112,890 A | 5/1992 | Behrens et al. | |
| 5,204,473 A | 4/1993 | Winter et al. | |
| 5,240,975 A | 8/1993 | Winter et al. | |
| 5,362,881 A | 11/1994 | Leistner et al. | |
| 5,554,760 A | 9/1996 | Winter et al. | |
| 5,563,242 A | 10/1996 | Winter et al. | |
| 5,574,166 A | 11/1996 | Winter et al. | |
| 5,576,141 A | 11/1996 | Neumann et al. | |
| 5,977,219 A | 11/1999 | Ravichandran et al. | |
| 6,166,218 A | 12/2000 | Ravichandran et al. | |
| 6,451,887 B1 | 9/2002 | Wood et al. | |
| 7,847,103 B2 * | 12/2010 | Chang | ............ 548/255 |
| 2002/0013462 A1 | 1/2002 | Gupta et al. | |
| 2003/0064303 A1 | 4/2003 | Nishimura et al. | |
| 2010/0086500 A1 | 4/2010 | Chang | |

OTHER PUBLICATIONS

Li et al., J. Polymer Science: Polymer Chemistry Edition, vol. 21, 1983, pp. 1263-1271.*
Patani, et al., Chem. Rev., 1996, vol. 96, pp. 3147-3176, esp. p. 3152.*
Xiao-Bai Li, M. Winnik and J. Guillet, Photocleavage of the acetate of a hyroxyphenyl benzotriazoleUV absorrber. , J Polymer Science, vol. 21, 1263-1271 (1983).
Byung Hee Kim and Dong Joon Choo, Synthesis and polymerization of UV stabilizing monomers, Bull. Korean Chem Soc. vol. 14, 651 (1993).
PCT/US 09/05392—Search Report and Written Opinion of International Searching Authority Mailed Feb. 1, 2010.

* cited by examiner

Primary Examiner — Susannah Chung
(74) Attorney, Agent, or Firm — Michael P. Aronson (57) ABSTRACT

The invention relates to ultraviolet light absorbing compounds, their preparation and uses as protective agents and stabilizers in coatings, plastics and topically applied products. The compounds are ketone derivatives of 2-(2-hydroxyphenol)benzotriazole of formula I,

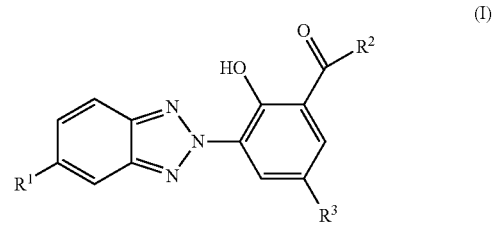

(I)

where $R^1$ is hydrogen atom, or a halogen atom, or a straight-chain or branched lower alkyl or lower alkoxy of 1 to 4 carbon atoms; $R^2$ is an unsubtituted or substituted aryl group or an unsubstituted or substituted straight-chain or branched alkyl having 1 to 18 carbon atoms or a cycloaliphatic group having 5 to 6 carbon atoms; and $R^3$ is a straight-chain or branched alkyl or alkylaryl group or alkoxyl or phenyl or phenyl substituted with alkyl, cycloalkyl, carboalkoxy, chlorine or arylalkyl groups.

12 Claims, 2 Drawing Sheets

ULTRAVIOLET LIGHT ABSORBING KETONES OF 2-(2-HYDROXYPHENYL) BENZOTRIAZOLE

This is a Continuation of co-pending U.S. patent application Ser. No. 12/286,921 filed Oct. 4, 2008, incorporated herein in its entirety, by reference.

FIELD OF INVENTION

The invention relates to ultraviolet light absorbers useful as protective agents and stabilizers in coatings, plastics and topically applied products. More particularly, the invention concerns compounds which are ketone derivatives of 2-(2-hydroxyphenol)benzotriazole and to compositions containing these UV absorbing ketones.

BACKGROUND OF INVENTION

A problem in the art of manufacturing and processing thermoplastic polymers and coating compositions is their instability upon extended exposure to ultraviolet (UV) light sources. It is well known that light, oxygen and heat cause degradation of polymers resulting in deterioration of mechanical and physical properties of the polymer. Coatings and plastics tend to demonstrate unwanted color changes and reduced mechanical strength upon exposure to UV radiation. To prevent or at least retard the damage caused by these factors, UV light absorbing compounds are added to the plastic as stabilizers.

Benzotriazoles have long been an important class of UV absorbers and have gained wide commercial importance and acceptance as UV stabilizers for many industrial applications. The prior art is replete with references to their manufacture and utility. For example:

U.S. Pat. No. 3,004,896 to Heller et al demonstrated that hydroxyphenyl benzotriazoles possess desirable overall absorption characteristics for application involving the protection of UV light absorbing polymer compositions since they absorb very strongly within the UV region but absorbed very little light as the wavelength approaches 400 nm, i.e., are colorless or non-actinic in the visible spectrum.

U.S. Pat. No. 4,275,004 to Winter et al discloses a high caustic coupling process for preparing o-nitroazobenzene intermediates useful in the synthesis of 2-aryl-2H-benzotriazole light absorbers.

There are a variety of considerations when choosing a suitable UV light stabilizer. Compatibility is one of them. Many stabilizers prove to be incompatible with the polymer or coating composition being stabilized. Another important consideration is the volatility of the stabilizer in the polymer and during its processing. The stabilizer must have sufficiently high molecular weight so that it remains in the polymer matrix for the life of the plastic or coating. Many polymers are processed at very high temperatures which causes the stabilizer to vaporize.

To improve polymer compatibility and reduce volatility, appropriate side chains have been added to the phenolic ring or the benzene ring of the benzotriazole. For example, U.S. Pat. Nos. 4,226,763 and 4,278,589 to Dexter et al disclose 2-(2-hydroxyphenol)benzotriazoles substituted ortho and/or para to the hydroxyl group by cumyl or substituted cumyl groups.

U.S. Pat. No. 3,766,205 to Heller et al describes 2-(2-hydroxyphenol)benzotriazole light stabilizers having methyl and carbododecyloxyethyl groups ortho and para to the hydroxy group which are employed, for example, in polyamides and polyesters.

Japanese Patent Application Sho 54-95,233 describes 2-(2-hydroxyphenol)benzotriazole light stabilizers having tert.butyl groups ortho and para to the hydroxyl group which are employed together with co-stabilisers in materials for colour photography.

U.S. Pat. Nos. 4,853,471 and 5,032,498 to Rody et al disclose 2-(2-hydroxyphenol)benzotriazole UV absorbers having tert.butyl groups and —$CH_2CH_2COOR$ acid or ester groups ortho and para respectively to the hydroxy group which are used in particular for stabilizing and improving lacquers and photographic material. The compounds can be either monomers or ester linked dimers of the substituted 2-(2-hydroxyphenol)benzotriazole.

U.S. Pat. Nos. 5,554,760 and 5,574,166 to Winter et al discloses a soluble, crystalline form of 2-(2-hydroxyphenol) benzotriazole which is substituted in the 3-position (ortho to the hydroxyl group) with an α-cumyl group and in the 5-position (para) usually with a mixture with various alkylated moieties as substituents or as single compounds substituted with one bulky, tert-alkyl group.

U.S. Pat. Nos. 5,977,219 and 6,166,218 to Ravichandran et al disclose 2-(2-hydroxyphenol)benzotriazole monomers and dimers which are substituted at the 5-position of the benzo ring by an electron withdrawing group. The compounds are claimed to exhibit enhanced durability and low loss rates when incorporated into automotive coatings particularly when the 3-position of the phenyl ring is also substituted by phenyl or phenylalkyl, e.g., 5-trifluoromethyl-2-(2-hydroxy-3-α-cumyl-5-tert-octylphenyl)-2H-benzotriazole.

U.S. Pat. No. 5, 240,975 to Winter et al discloses liquid substituted 2H-benzotriazole mixtures prepared by alkylation with concomitant dealkylation, fragmentation and realkylation of 2-(2-hydroxy-5-alkylphenyl)-2H-benzotriazoles or of 2-(2-hydroxy-3,5-dialkylphenyl)-2H-benzotriazoles with straight or branched alkenes of 8 to 30 carbon atoms in the presence of an acid catalyst at 100-200° C.

Since the types of UV light sensitive polymers and compositions employed in different applications is diverse there is not a single set of side chain substituents or "modifying groups" that will provide an optimal set of properties for these diverse chemical systems. Furthermore, in most cases the modifying groups do not add substantially to the UV absorption characteristics of the molecule, such that the additional molecular weight of the modifying group does not contribute to the light absorption properties of the UV light stabilizer. Consequently, the UV absorption properties of the modified stabilizer can actually be reduced because of a relative lowering in molar extinction coefficient.

One approach to improve the level and efficiency of UV light protection has involved the use of combinations of materials. For example:

U.S. Pat. No. 3,496,136 to Susi et al disclosed a combination of UV absorbers and substituted melamine derivatives as stabilizers for rigid thermoplastic resins such as PVC or polystyrene.

U.S. Pat. Nos. 4,413,933 and 4,426,471 to Berner discloses the use of various sterically hindered amine light stabilizers such as N-substituted 2,2,6,6-tetraalkylpiperadine compounds, their acid addition salts or complexes with metal compounds, optionally together with further stabilizers, especially substituted hydroxyphenyl benzotriazoles, for stabilizing acid catalyzed stoving lacquers.

Several studies have attempted to make UV absorbers more efficient and/or effective by introducing different substituents or by coupling known UV chromophores to the benzotriazole which could increase intrinsic absorption. For example:

U.S. Pat. No. 3,936,418 to Pond et al discloses benzotriazole ortho-ester ultraviolet light stabilizers and their use in organic compositions. Specifically, substituted 2-(2-hydroxyphenol)benzotriazole were reacted with aryl acid chlorides, e.g., benzoyl chloride or isophthaloyl chloride, to form an ortho ester, i.e., esterification of the 2-hydroxy group of the phenyl ring. The use of di- or tri-functional aryl carboxylic acids produced multimer esters of 2-(2-hydroxyphenol)benzotriazole. No data was disclosed on the UV absorption efficiency of the ortho esters or a comparison with other hydroxyphenyl benzotriazoles.

U.S. Pat. No. 5,362,881 to Leistner et al found that the volatility of benzotriazole and benzophenone stabilizers can be sharply reduced by coupling these different UV light absorbing chemical moieties utilizing a methylene bridge. The UV absorber obtained is composed of a discrete benzotriazole moiety and a discrete benzophenone moiety joined by a methylene group. The UV light absorption characteristics of the molecules were not reported.

As requirements for durability, effectiveness and use of certain solvents become ever more stringent and demanding, the search for still more stable, durable, more effective and efficient UV stabilizers continues. Furthermore, because of the diversity of polymer systems employed in plastics and coatings there is also a continuing need for versatile process chemistry that can provide a suite of ultra-violet light absorbing compounds which can be tailored to different polymer applications.

It has now been found that a range of ketones of 2-(2-hydroxyphenyl)benzotriazoles having an acyl group substituted ortho to the hydroxy group of the phenyl ring can be efficiently prepared. Surprisingly, the ketone substituents were found to increase UV absorption and did not lead to a decrease in absorption as has been found for bulky 3' alkyl groups in 2-(3'-alkyl-2'hydroxyphenyl)benzotriazoles and the 2-hydroxyphenyl naphthotriazoles (e.g., U.S. Pat. No. 4,129,521 to A. Strobel). The UV absorbers of the present invention have structural elements contained in both 2-(2-hydroxyphenyl)benzotriazoles and hydroxybenzophenones. In particular, the adjacency of the hydroxyl and keto groups on the "central" phenyl ring provides a "hybrid" structure which allows for hydrogen bonding between these groups and is believed to lead to the increased UV absorption characteristics of the compounds which improves their efficiency and spectral coverage.

In some hybrid variants in which the ketone bridges a 2-(2-hydroxyphenyl)benzotriazole and a benzene ring the compounds have UV absorption characteristics of a benzotriazole and a benzophenone. That is, the middle hydroxyphenyl group is shared between the benzotriazole and the phenone.

As such the ketone substituents of the instant compounds not only influences physical properties such as melting point but also provides enhanced UV absorption efficiency, i.e., molar extinction coefficient and broader coverage across the UV A and B spectrum.

SUMMARY OF THE INVENTION

The invention provides ultraviolet light absorbing compounds having formula I:

wherein $R^1$ is Hydrogen or a halogen atom or a straight-chain or branched lower alkyl or lower alkoxy of 1 to 4 carbon atoms;

$R^2$ is a unsubtituted or substituted aryl group or an unsubstituted or substituted straight-chain or branched alkyl group having 1-30 carbon atoms, preferably 1 to 18 carbon atoms or an unsubstituted or substituted cycloaliphatic group having 5 to 6 carbon atoms; and R3 is a straight-chain or branched alkyl of 1 to 14 carbon atoms, preferably 1 to 8 carbon atoms and most preferably 1 to 5 carbon atoms or alkylaryl group of 7 to 12 carbon atoms or alkoxy of 1 to 4 carbon atoms or phenyl, phenyl substituted with an alkyl group, said alkyl groups having 1 to 8 carbon atoms or cycloalkyl group having 5 to 6 carbon atoms or carboalkoxy group having 2 to 9 carbon atoms or chlorine or an arylalkyl group having 7 to 9 carbon atoms.

The invention further encompasses compositions of matter which include the ultraviolet light absorbing compound having formula (I). One embodiment of such a composition is an ultraviolet light (UV) absorbing compositions that includes a carrier and from 0.01% to 10% of the UV light absorbing ketone of formula (I). These compositions function as a protective coating or film when applied to a substrate which is susceptible to UV damage.

In another embodiment, the composition of matter includes an organic material which is subject to UV light-induced deterioration, e.g., a plastic, in combination with from 0.1% to 10%, preferably 0.1% to 5% by weight of the UV light absorbing ketone of formula (I).

The invention also encompasses a process for the preparation of the UV light absorbing compounds in which a preformed 2H-benzotriazole is reacted with an appropriate acylating agent such as an acid, an acid halide (e.g., an acid chloride) or an anhydride to form the instant ketones.

These and other variations of the inventive compounds, process and compositions disclosed herein will become clear from the description of the invention which follows.

BRIEF DESCRIPTION OF DRAWINGS

FIG. 2 is a graph comparing the UV absorption spectra of compound 1 (2-(2-hydroxy-3-benzoyl-5-methyl-phenyl)

benzotriazole, Curve A) with the absorption spectra of compound 4 (2-(2-Hydroxy-3-Acetyl-5-Methyl-phenyl)Benzotriazole, Curve E) and compound 5 (2-(2-Hydroxy-3-nonanoyl-5-Methyl-phenyl)Benzotriazole, Curve F) and described in Example 4.

DETAILED DESCRIPTION OF THE INVENTION

Unless otherwise indicated, % or wt % as used herein refers to percent by weight of an ingredient as compared to the total weight of the composition or component that is being discussed.

Except in the operating and comparative examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

For the avoidance of doubt the word "comprising" is intended to mean "including" but not necessarily "consisting of" or "composed of." In other words, the listed steps or options need not be exhaustive.

The invention relates to ultraviolet light (hereinafter designated "UV") absorbing compounds, their preparation and specific types of compositions which incorporate these compounds. The UV absorbing compounds and compositions in which they are incorporated are described in detail below including preferred embodiments and optional and alternative ingredients.

UV Absorbing Compounds

The UV absorbing compounds of the invention are ketones in which the acyl group is adjacent (designated the "3 position") to the hydroxyl group of the 2-(2-hydroxyphenyl)-benzotriazole. The compounds have the formula (I):

$R^1$ is a halogen atom, a straight-chain or branched lower alkyl or a lower alkoxy of 1 to 4 carbon atoms.

$R^2$ is a substituted or unsubtituted aryl group or an unsubstituted or substituted straight-chain or branched alkyl group having 1-30 carbon atoms, preferably 1 to 18 carbon atoms or an unsubstituted or substituted cycloaliphatic group having 5 to 6 carbon atoms.

For purposes of this invention the term "aryl" is defined as an aromatic hydrocarbon moiety.

An aryl group preferably contains 6 to 12 carbon atoms and may include for example phenyl, naphthyl, naphthyl, biphenyl and phenanthryl groups. The aryl group is preferably a phenyl group.

$R^3$ is a straight-chain or branched alkyl of 1 to 14, preferably 1 to 8, more preferably 1 to 5 carbon atoms or alkylaryl group of 7-12 carbon atoms or alkoxy of 1 to 4 carbon atoms or phenyl or phenyl substituted with alkyl groups, said alkyl groups having 1 to 8 carbon atoms or cycloalkyl of 5 to 6 carbon atoms or carboalkoxy of 2 to 9 carbon atoms or chlorine or arylalkyl of 7 to 9 carbon atoms.

$R^1$ can be a lower alkyl of 1 to 4 carbon atoms such as methyl, ethyl or n-butyl. $R^1$ can be halides such as chlorine, $R^1$ can also be lower alkoxy of 1 to 4 carbon atoms such as methoxy, ethoxy or n-butoxy. $R^1$ can also be carboalkoxy of 2 to 9 carbon atoms such as carbomethoxy, carboethoxy, or carbo-n-octoxy.

Preferably $R^1$ is hydrogen or halides or lower alkyl of 1 to 2 carbon atoms or methoxy.

Most preferably $R^1$ is hydrogen or chlorine.

$R^2$ can be either an unsubstituted or substituted phenyl group.

$R^2$ can be a phenyl group substituted by a straight-chain or branched alkyl groups having 1 to 8 carbon atoms such as methyl, ethyl, propyl, isopropyl or tert.butyl groups.

$R^2$ can be a phenyl group substituted by an alkoxy group having 1 to 4 carbon atoms such as methoxy, ethoxy, n-butoxy.

$R^2$ can be a phenyl group substituted by a carboxyalkyl group having 1 to 4 carbon atoms such as carboxymethyl, carboxyethyl, or carboxybutyl.

$R^2$ can be a phenyl group substituted by a carboalkoxy group having 2 to 9 carbon atoms such carbomethoxy, carboethoxy, carbo-n-butoxy, or carbo-n-octoxy.

$R^2$ can be a phenyl group substituted by a carboxyl group.

$R^2$ can be a straight-chain or branched alkyl having 2 to 30, preferably 1 to 18 carbon atoms, preferably 2 to 8 carbon atoms, preferably 2 to 5 carbon atoms.

$R^2$ can be a straight-chain or branched alkyl having 1-30 carbon atoms, preferably 1 to 18 carbon atoms, preferably 1 to 8 carbon atoms, preferably 1 to 5 carbon atoms substituted with an alkoxy group having 1-8 carbon atoms such as methoxy, ethoxy or tert.butoxy, or substituted with a carboxyl group or substituted with a phenyl group.

$R^2$ can be for example methyl, ethyl, butyl, hexyl, octyl, nonyl, tert.butyl, amyl, tert.octyl, 2 ethylhexyl, cumyl or carboxyl.

$R^2$ can be a cycloaliphatic group having 5 to 6 carbon atoms such as cyclohexyl or a cycloaliphatic group substituted with an alkyl or alkoxyl group having 1-8 carbon atoms;

Preferably $R^2$ is a phenyl group or an alkyl group having 1 to 5 carbon atoms or a cyclohexyl group.

$R^2$ can be an unsubstituted straight-chain or branched alkyl having 1 to 9 carbon atoms; a straight-chain or branched alkyl having 1 to 9 carbon atoms substituted with an alkoxyl group having 1 to 8 carbon atoms or a carboxyl group; a cyclohexyl group, or a cyclohexyl group substituted with an alkyl group having 1 to 4 carbon atoms or a cyclohexyl group substituted with an alkoxyl group having 1 to 4 carbon atoms.

$R^3$ can be alkyl of 1 to 12 carbon atoms, preferably 1 to 6 and most preferably 1-5 carbon atoms such as methyl, ethyl, sec-butyl, tert-butyl or amyl.

$R^3$ can also be alkoxy of 1 to 5 carbon atoms such as methoxy, ethoxy or n-butoxy. $R^3$ can also be phenyl substituted with alkyl groups, said alkyl groups having 1 to 5 carbon atoms such as methyl, tert-butyl, or tert-amyl. $R^3$ can also be cycloalkyl of 5 to 6 carbon atoms such as cyclopentyl or cyclohexyl. $R^3$ can also be carboalkoxy of 2 to 5 carbon atoms such as carbomethoxy, carboethoxy, carbo-n-butoxy. $R^3$ can also be arylalkyl of 7 to 9 carbon atoms such as benzyl, α-methyl benzyl or α,α-dimethyl benzyl.

$R^3$ can be a straight-chain or branched alkyl of 1 to 5 carbon atoms or an alkylaryl group having about 7 to about 12 carbon atoms or an alkoxy of 1 to 4 carbon atoms or phenyl group or a phenyl group substituted with alkyl groups, said alkyl groups having 1 to 8 carbon atoms or a cycloalkyl group of 5 to 6 carbon atoms or a carboalkoxy group of 2 to 9 carbon atoms or chlorine or an arylalkyl group of 7 to 12 carbon atoms.

Preferably $R^3$ is alkyl of 1 to 5 carbon atoms, cyclohexyl, phenyl, α-methylbenzyl, α,α-dimethylbenzyl (i.e., cumyl) or amyl.

preferably $R^3$ is methyl, tert-butyl, tert-amyl, sec-butyl, cyclohexyl, carboxyethyl, α-methylbenzyl or α,α-dimethylbenzyl.

The convention used throughout in the naming of specific compounds falling with the scope of the invention is to treat them as derivatives of 2-(2-hydroxy phenyl)-benzotriazoles wherein the ketone group is a component of the substituent located at the 3 position on the phenyl ring.

One embodiment of the compounds of the invention have a structure represented by formula V:

(V)

where $R^1$ and $R^3$ have the meanings defined above and $R^4$ is hydrogen or a straight-chain or branched alkyl groups having 1 to 8 carbon atoms, preferably 1 to 6 carbon atoms, more preferably 1-4 carbon atoms or an alkoxy group having 1 to 4 carbon atoms or a carboxyalkyl group having 2 to 9 carbon atoms or a carboalkoxy group having 2 to 9 carbon atoms or a carboxyl group.

Compounds represented by formula V are hybrid structures of benzotriazole and benzophenone, which are both strong UV chromophores. The UV spectrum of the compounds provides a broad absorption between 280 and about 350 nm with spectral features characteristic of both components. In contrast to the methylene coupled benzophenone-benzotriazole compounds disclosed by Leistner et al, the hybrid structures represented by formula I of the invention have only a single hydroxyphenyl group which is "shared" between the triazole and benzoyl groups.

Figure 1:
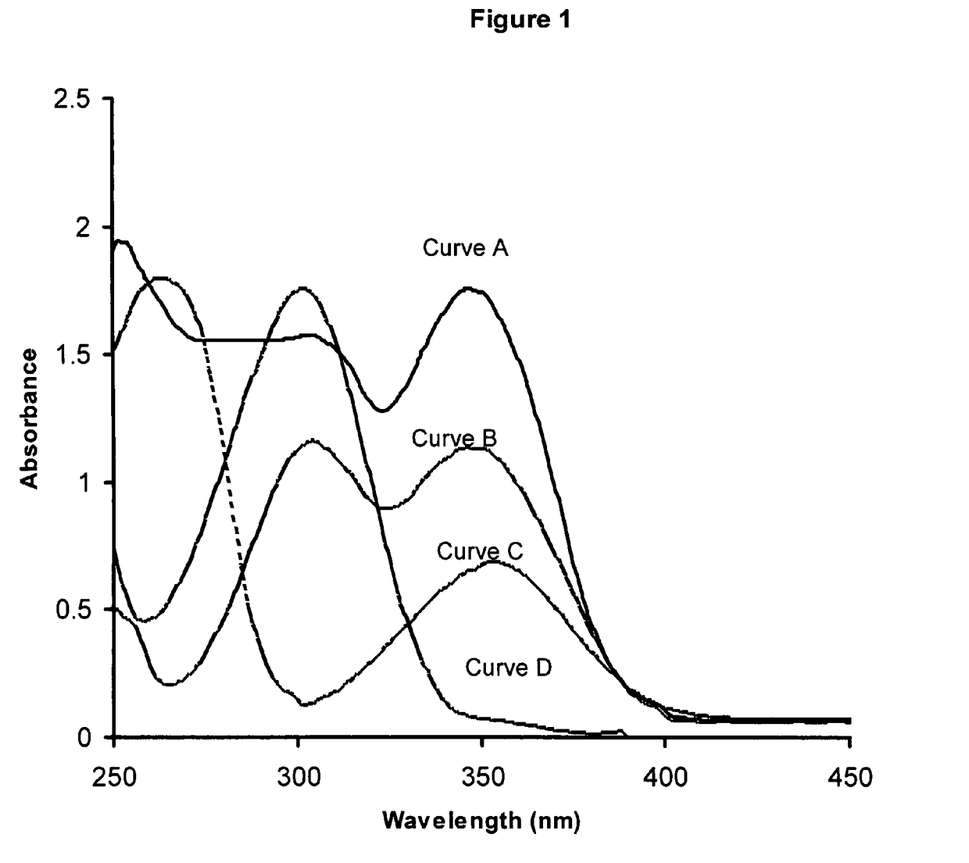
FIG. 1 is a graph comparing the UV absorption spectra of a compound of the invention, compound 1 (2-(2-hydroxy-3-benzoyl-5-methyl-phenyl)benzotriazole, Curve A) with a prior art UV absorbers 2-(2-hydroxy-3-cumyl-5-tert.Octylpheny)benzotriazole (Curve B), and 2-hydroxy 5-methyl benzophenone (Curve C) and an ester intermediate which is a precursor of compound 1 (Curve D) as described in Example 1.

Because of the sharing of the central phenol, the molecules represented by formula V have significantly higher mass UV extinction coefficient(s) and a broader absorption(s) over the UVA and UVB spectra (FIG. 1, Curve A) than prior art benzotriazoles (FIG. 1 Curve B). This unique molecular feature makes the hybrid variants of the invention (i.e., compounds having formula V) highly efficient UV absorbers.

A preferred variant of formula V has $R^1$=H or Cl; $R^4$ is hydrogen or a lower alkyl or lower alkoxyl having in both cases 1 to 4 carbon atoms and $R^3$ is methyl or ethyl or tert.butyl or amyl or cumyl.

The following are typical representatives of compounds of formula I in which $R^2$ is an aryl or substituted aryl group falling within formula V: 2-[2-hydroxy-3-benzoyl-5-methyl-phenyl]-benzotriazole or 2-[2-hydroxy-3-benzoyl-5-isopropyl-phenyl]-benzotriazole or 2-[2-hydroxy-3-benzoyl-5-tert.butyl-phenyl]-benzotriazole or 2-[2-hydroxy-3-benzoyl-5-tert.butyl-phenyl]-5-chlorobenzotriazole or 2-[2-hydroxy-3-benzoyl-5-cumyl-phenyl]-benzotriazole or 2-[2-hydroxy-3-benzoyl-5-cumyl-phenyl]-5-chlorobenzotriazole or 2-[2-hydroxy-3-(3'-isopropyl benzoyl)-5-tert.butyl-phenyl]-benzotriazole or 2-[2-hydroxy-3-benzoyl-5-amyl-phenyl]-benzotriazole or 2-[2-hydroxy-3-(3'-methyoxy-benzoyl)-5-tert.butyl-phenyl]-benzotriazole or 2-[2-hydroxy-3-(3'-methyl benzoyl-5-tert.butyl]-benzotriazole or 2-[2-hydroxy-3-(3'-methyoxy-benzoyl)-5-methyl-phenyl]-benzotriazole.

When $R^2$ is unsubstituted or substituted straight-chain or branched alkyl having 1-30 carbon atoms, preferably 1 to 18 carbon atoms or a cycloaliphatic group having 5 to 6 carbon atoms the compounds retain the hybrid "phenone" structural element (keto group adjacent to the hydroxyl group of the phenyl ring) and provided enhanced UV absorption characteristics.

The following are typical representatives of such hybrid compounds of formula I in which $R^2$ is unsubstituted or substituted straight-chain or branched alkyl having 1 to 18 carbon atoms or a cycloaliphatic group having 5 to 6 carbon atoms or 2-[2-hydroxy-3-acetyl-5-methyl-phenyl]-benzotriazole or 2-[2-hydroxy-3-propanoyl-5-methyl-phenyl]-benzotriazole or 2-[2-hydroxy-3-(2',2' dimethyl propanoyl)-5-methyl-phenyl]-benzotriazole or 2-[2-hydroxy-3-(1' carboxy propanoyl)-5-methyl-phenyl]-benzotriazole or 2-[2-hydroxy-3-(1'-carboxy-1-methyl-propenoyl)-5-methyl-phenyl]-benzotriazole or 2-[2-hydroxy-3-cyclohexanoyl-5-methyl-phenyl]-benzotriazole or 2-[2-hydroxy-3-acetyl-5-tert.butyl-phenyl]-benzotriazole or 2-[2-hydroxy-3-propanoyl-5-tert.butyl-phenyl]-benzotriazole or 2-[2-hydroxy-3-(2',2' dimethyl propanoyl)-5-tert.butyl-phenyl]-benzotriazole or 2-[2-hydroxy-3-(1' carboxy propanoyl-5-tert.butyl-phenyl]-benzotriazole or 2-[2-hydroxy-3-(1' carboxy propenoyl)-5-tert.butyl-phenyl]-benzotriazole or 2-[2-hydroxy-3-cyclohexanoyl-5-tert.butyl-phenyl]-benzotriazole or 2-[2-hydroxy-3-acetyl-5-cumyl-phenyl]-benzotriazole or 2-[2-hydroxy-3-propanoyl-5-cumyl-phenyl]-benzotriazole or 2-[2-hydroxy-3-(2',2' dimethyl propanoyl)-5-cumyl-phenyl]-benzotriazole or 2-[2-hydroxy-3-(1' carboxy propanoyl-5-cumyl-phenyl]-benzotriazole or 2-[2-hydroxy-3-cyclohexanoyl-5-cumyl-phenyl]-benzotriazole or 2-[2-hydroxy-3-acetyl-5-methyl-phenyl]-5-chlorobenzotriazole or 2-[2-hydroxy-3-propanoyl-5-methyl-phenyl]-5-chlorobenzotriazole or 2-[2-hydroxy-3-(2',2' dimethyl propanoyl)-5-methyl-phenyl]-5-chlorobenzotriazole or 2-[2-hydroxy-3-(1' carboxy propanoyl)-5-methyl-phenyl]-5-chlorobenzotriazole or 2-(2-hydroxy-3-nonanoyl-5-methyl)benzotriazole.

Synthesis

The invention further provides processes for the preparation of the benzotriazole ketones of formula I by, in the presence of strong acids or Lewis acids or acylium ion salts, the reaction of a 2-benzotriazolyl-4-substituted phenol with an acylating agent such as acid halides, acids and anhydrides.

Suitable acid halides are acid chlorides. Suitable acid chlorides may include for example, an unsubstituted or substituted benzoyl chloride, a unsubstituted or substitutes alkanoyl chloride, cylclohexanoyl chloride, substituted cylclohexanoyl chloride and mixtures thereof.

Suitable anhydrides may for example include acetic anhydride. Benzoic anhydride and succinic anhydride might also be suitable under certain conditions.

When the alkyl group of the alkanoyl chloride contains more that about 7 to 8 carbon atoms or is branched, the possibility exists for the chains to break into smaller fragments or to isomerize. This process, which can lead to a statistical mixture of substituents, results in mixtures of compounds with different $R^2$ substituents, i.e., different chain lengths or isomeric structures. Such mixtures may still be useful UV absorbers and in fact may have beneficial properties such as lower melting points or reduced crystallinity, e.g. exist as liquids (see also below). To the extent to which such compounds are useful as UV light stabilizers, they are within the scope of the invention.

The process is illustrated below with the reaction of 2-benzotriazolyl-4-methyl phenol (Formula VI) with benzoyl chloride to yield 2-[2-hydroxy-3-benzoyl-5-methyl-phenyl]-benzotriazole (Formula V) according to the reaction given below. An illustration of the method to prepare ketones using an alkyl acid chloride is given in Example 4.

The process conditions and intermediates of course depend upon the UV absorbing variant desired. Other compounds of the invention can be prepared in an analogous manner using for example, appropriately substituted 2-benzotriazolyl-4-hydrocarbyl phenol and appropriately substituted acid chlorides or under suitable conditions other acylating agents to yield the range of UV absorbing compounds disclosed above.

The overall reaction in this case can be represented as (or I in the general case)

In contrast to the synthesis of ortho-esters of benzotriazoles disclosed in U.S. Pat. No. 3,936,418 which was carried out for 15 hrs at 50-60° C. in a single step, the current process proceeds in two steps one or both of which are carried out at a higher temperature and results in very different structures having surprisingly superior UV absorption properties (see below).

The first step can be carried out in an aprotic solvent such as methylene chloride, toluene, benzene, xylene, hydrocarbons such as hexane, heptane, petroleum ethers, and mineral spirits, cycloaliphatic ethers such as furan, tetrahydrofuran and dioxane.

The benzotriazole, acid chloride e.g., benzoyl chloride, acid catalyst (e.g., AlCl$_3$) and optional solvent are combined and heated under reflux conditions at atmospheric pressure. The ratio of benzotriazole and acid chloride is in the range from about 3:1 to about 1:3, preferable about 3:1 to about 1:1.5.

The hydroxyphenyl benzotriazole reactant may be prepared by any method known in the art including those taught in U.S. Pat. Nos. 5,097,041, 4,943,637 and 5,104,992. 2-aryl-2H-benzotriazoles monomers may be produced by reducing o-nitroazobenzenes through a 2-phenylbenzotriazole-N-oxide intermediate. A wide variety of reduction techniques is known. Reduction of o-nitroazobenzenes to 2-phenylbenzotriazole by zinc in the presence of sodium hydroxide is disclosed in U.S. Pat. Nos. 3,018,269; 3,230,194; 3,773,751; 4,041,044; and 4,224,451. Reduction using aldehyde reducing agents and aromatic ketone catalysts is disclosed in U.S. Pat. No. 4,835,284. Reduction using saccharides and an aromatic ketone catalyst is disclosed in U.S. Pat. No. 4,780,541. All of these patents are incorporated herein by reference. These show methods for the preparation of hydroxyphenyl benzotriazoles by reductive cyclization of azo dyes with saccharides in the presence of aromatic ketone catalysts, which act by receiving hydrogen from the reducing agent and giving hydrogen to a material to be reduced. In each of these cases, saccharide reduction is catalyzed by such aromatic ketone catalysts as substituted and unsubstituted fluorenone.

In the second step, the solvent is removed by distillation and the temperature is increased (e.g., to 160° C.). It is believed this step initiates a Fries rearrangement of any ester which may have formed in step 1 to form the desired ketone through the migration of the acyl group (e.g., the benzoyl group) to the ortho position relative to the hydroxy group since the para position is blocked by R$^3$ which must be a substituent other than H since substitution at the para position is not desirable.

It should be noted that non-aromatic organic solvents with high boiling points are also suitable as a solvent for steps 1 and 2. If such a solvent is used in the preparation of the compounds of the invention, there is no need to remove the solvent before Fries rearrangement is initiated. Such solvents include but not limited to dimethylsulfoxide, ethylene glycol monoacetate, ethylene glycol diacetate and diethylene glycol monobutyl ether).

The temperature of the reaction mixture formed in step 2 is then lowered to below about 90° C. and enough water is added until the cessation of bubbling.

The product formed in the above reaction (Formula V) can then be optionally purified by successive extractions in which esters that may be present in the product mixture are hydrolyzed, converted to water soluble variants by hydrolysis and extracted into an aqueous phase. Aqueous HCl is first added to the organic phase and the mixture stirred under reflux conditions. The mixture is then cooled and the aqueous layer discharged. Aqueous NaOH is then introduced to the organic phase, the mixture again stirred at reflux conditions, cooled and the aqueous phase is again discharged. Another portion of aqueous HCl is then added to the organic phase, the mixture again refluxed under shear, cooled and the aqueous phase again discharged. Finally, the remaining organic phase is washed several times to obtain the target ketone.

Four methods are used to identify the product and purity: i) UV spectroscopy to confirm that the UV spectrum contains both the characteristic double absorption peaks of 2-(2-hydroxy phenyl)benzotriazole at about 310 and 345 nm and the significant hydroxy benzophenone spectral features between 300 and about 250 nm; ii) proton NMR assignments to confirm the presence of the hydroxy group and the two types of phenyl protons in the case of the benzoyl varient; iii) gas chromatography which demonstrates a single GC peak having a longer retention time, compared to reactant, or ester intermediate, and is consistent with the ketone; and iv) isolation of the ester intermediate (precursor of compound 1) after the first step but before the high temperature treatment (second step) which does not exhibits the bimodal UV absorption spectra typical of benzotriazole or benzophenone moiety. The results of these methods are illustrated in Example 1 below.

For certain applications it is desirable to employ mixtures of the UV absorbing compounds having Formula I in which the individual components of the mixture differ in one or more of the R$^1$, R$^2$ or R$^3$ substituent groups. For example, when R² is an alky group it is possible to reduce the tendency of the UV absorbing compound to crystallize from an organic solvent or polymer melt by utilizing a mixture of different UV compounds having different R² alkyl chain lengths, isomers or degree of branching. Such mixtures can display improved compatibility (e.g., solubility) especially in a polymer film or plastic.

To obtain mixtures of the UV absorbing compounds which differ in one or more of the R¹, R² or R³ substituent groups the different components of the mixture can of course be separately synthesized. However, in some cases it is convenient to form the mixture in situ by employing mixtures of different benxotriazole phenol and acid chloride reactants. The use of such mixed reactants in the synthesis described above to form mixtures of UV absorbing compounds having beneficial solubility; absorption or other physical or chemical properties is considered to be within the scope of the invention.

It should be pointed out that the starting benzotrazole can include 2-(2-hydroxy-5-methylphenyl)-2H-benzotriazole in contrast to the alkylation process taught in U.S. Pat. No. 5,240,975 although alkyl groups having a greater number of carbon atoms can also be used.

Applications

The compounds of formula I are broadly useful in protecting materials from damage caused by exposure to ultraviolet radiation. The compounds according to the present invention can either be incorporated directly into the materials to be protected from UV light rays, e.g., in a plastic, or they can be incorporated into protective coatings, foils and coverings. The protected material or protective covering can contain, for example 0.001% to 15% of the active UV absorbing ingredient, preferably 0.1 to about 10%, preferably 0.01 to 5%. In non-actinic agents for the human skin, the content of active agent should be advantageously 0.1% to 10% calculated on the non-volatile components of the preparation.

One embodiment of the invention is a composition of mater comprising an organic material subject to light-induced deterioration stabilized with from 0.1 to 5% by weight of one or more of the ultraviolet light absorbing compounds of the invention as described above. The UV absorbing compounds of the invention are especially suitable for protecting organic materials that are synthetic polymer such polyesters, polycarbonates, polysulfones, polyamides, acrylic resins, polyolefins, polystyrenes, polyurethanes and various other polymers and blends described in more detail below. However, the organic material can also be a natural polymer such as cellulose based polymers, e.g., wood. The types of materials are discussed in more detail below.

The UV absorbing compounds of the invention are especially suitable when the composition of matter is a thermoplastic or thermosetting polymer. Such compositions are generally formed under high shear at elevated temperatures. Because the UV absorbing compounds of the invention are thermally stable and not volatile they are not lost during processing of the composition.

Suitable ultraviolet light absorbing compound for use in the above compositions include but are not limited to 2-[2-hydroxy-3-benzoyl-5-methyl-phenyl]-benzotriazole or 2-[2-hydroxy-3-benzoyl-5-isopropyl-phenyl]-benzotriazole or 2-[2-hydroxy-3-benzoyl-5-tert.butyl-phenyl]-benzotriazole or 2-[2-hydroxy-3-benzoyl-5-tert.butyl-phenyl]-5-chlorobenzotriazole or 2-[2-hydroxy-3-benzoyl-5-cumyl-phenyl]-benzotriazole or 2-[2-hydroxy-3-benzoyl-5-cumyl-phenyl]-5-chlorobenzotriazole or 2-[2-hydroxy-3-(3-isopropyl benzoyl)-5-tert.butyl-phenyl]-benzotriazole or 2-[2-hydroxy-3-benzoyl-5-amyl-phenyl]-benzotriazole or 2-[2-hydroxy-3-(3'-methyoxy-benzoyl)-5-tert.butyl-phenyl]-benzotriazole or 2-[2-hydroxy-3-(3'-methyl benzoyl-5-tert.butyl]-benzotriazole or 2-[2-hydroxy-3-(3'-methyoxy-benzoyl)-5-tert.butyl-phenyl]-benzotriazole or 2-[2-hydroxy-3 acetyl)-5-methyl-phenyl]-benzotriazole or 2-[2-hydroxy-3-propanoyl-5-methyl-phenyl]-benzotriazole or 2-[2-hydroxy-3-(2',2' di-methyl propanoyl)-5-methyl-phenyl]-benzotriazole or 2-[2-hydroxy-3-cyclohexanoyl-5-methyl-phenyl]-benzotriazole or 2-[2-hydroxy-3-(acetyl)-5-tert.butyl-phenyl]-benzotriazole or 2-[2-hydroxy-3-propanoyl-5-tert.butyl-phenyl]-benzotriazole or 2-[2-hydroxy-3-(2',2' dimethyl propanoyl)-5-tert.butyl-phenyl]-benzotriazole or 2-[2-hydroxy-3-cyclohexanoyl-5-tert.butyl-phenyl]-benzotriazole or 2-[2-hydroxy-3-(acetyl)-5-cumyl-phenyl]-benzotriazole or 2-[2-hydroxy-3-propanoyl-5-cumyl-phenyl]-benzotriazole or 2-[2-hydroxy-3-propanoyl-5-cumyl-phenyl]-benzotriazole or 2-[2-hydroxy-3-(2',2' dimethyl propanoyl)-5-cumyl-phenyl]-benzotriazole or 2-[2-hydroxy-3-acetyl-5-methyl-phenyl]-5-chlorobenzotriazole or 2-[2-hydroxy-3-propanoyl-5-methyl-phenyl]-5-chlorobenzotriazole or 2-[2-hydroxy-3-propanoyl-5-methyl-phenyl]-5-chlorobenzotriazole or 2-[2-hydroxy-3-(2',2' dimethyl propanoyl)-5-methyl-phenyl]-5-chlorobenzotriazole or 2-(2-hydroxy-3-nonanoyl-5-methyl)benzotriazole.

Another embodiment of the invention comprises an ultraviolet light absorbing composition including a carrier, and 0.01% to 10%, preferably 0.1% to 5% by weight of an ultraviolet light absorbing compound of formula I which is uniformly dispersed in the carrier.

The term "carrier" is used herein to broadly encompass any suitable material or combination of materials that comprise a protective coating, foil, film, or covering over a substrate which is susceptible to damage from UV light exposure. The carrier need not and often is not itself resistant to UV damage and thus the compounds of the invention may be used to protect the integrity and properties of the coating, film, foil or covering itself which may serve a range of useful purposes beyond UV protection.

Suitable carriers can include one or more polymers, preferably film forming polymers, such as polyesters, polyester resins, polyamides, vinyl polymers, cellulose ethers, cellulose esters, polyurethanes polyhydrocarbons, acrylic polymers, various latex polymers and alkyd resins, polypeptides such as gelatin, and various mixtures thereof.

Alternatively, the ultraviolet light absorbing composition can be used to protect living tissue from UV radiation. In this case the carrier is a cosmetically acceptable material, i.e., safe for topical application to living tissue, generally human tissue such as cosmetically acceptable ointments, creams, lotions, gels, sprays and the like. Such carriers include oils and waxes such as hydrocarbon oils and waxes, e.g., mineral oil, vegetable oils and waxes such as triglycerides and ester oils, silicone oils and waxes, such as volatile silicones and polydimenthylsiloxanes, fluorocarbon oils, water (generally containing a compatibilizing agent) and mixtures thereof.

The compounds of this invention are effective stabilizers in combination with a wide range of organic polymers which are susceptible to damage from UV radiation. Polymers and their mixtures which can be stabilized include:

Mono- or diolefins, such as polyethylene, polypropylene, polyisobutylene, polymethylbutene-1, polymethylpentene-1, polyisoprene, polybutadiene and their copolymers; polystyrene and copolymers of styrene such as styrene/butadiene, styrene/acrylonitrile, styrene/acrylonitrile/methacrylate, styrene/acrylonitrile copolymers modified with acrylic ester; graft copolymers of styrene, for example the graft polymer of styrene to polybutadiene and acrylonitrile/butadiene/styrene or ABS plastics; halogen-containing vinyl polymers and copolymers such as polyvinyl chloride, polyvinylidene chloride, chlorinated rubbers, vinyl chloride/vinylidene chloride copolymers, vinyl chloride/vinyl acetate copolymers and vinylidene chloride/vinyl acetate copolymers; acrylic polymers such as polyacrylates and polymethacrylates, polyacrylic amides and polyacrylonitrile; copolymer of acrylic acid and one or more of its derivatives, and a melamine-formaldehyde resin; vinyl and allyl containing polymers and copolymers such as polyvinyl alcohol, polyvinyl acetate, polyvinyl stearate, polyvinyl benzoate, polyvinyl maleate, polyvinyl butyral, polyallyl phthalate, polyallyl melamine, ethylene/vinyl acetate; homopolymers and copolymers derived from epoxides such as for example polyethylene oxide or the polymers which are derived from bis-glycidyl ethers; polyacetals such as polyoxymethylene, polyoxymethylenes containing ethylene oxide; polyalkylene oxides such as polyoxyethylene, polypropylene oxide or polyisobutylene oxide; polyphenylene oxides; polyurethanes and polyureas, such as in urethane coatings; polycarbonates; polysulfones; polyamides and copolyamides such as polyamide 6, polyamide 6/6, polyamide 6/10, polyamide 11, polyamide 12, poly-m-phenylene-isophthalamide; polyesters such as polyethylene glycol terephthalate, poly-1,4-dimethylol-cyclohexane terephthalate, cross-linked polymers such as phenol/formaldehyde, urea/formaldehyde and melamine/formaldehyde resins; alkyd resins, such as glycerol/phthalic acid resins and mixtures thereof with melamine/formaldehyde resins; unsaturated polyesters resins which are derived from copolyesters of saturated and unsaturated dicarboxylic acids with polyhydric alcohols as well as from vinyl compounds as cross-linking agents and also the halogen-containing, flame-resistant modifications thereof; natural polymers, for example cellulose, rubber, as well as the chemically modified homologous derivatives thereof, for example cellulose acetates, cellulose propionates and cellulose butyrates and the cellulose ethers, for example methyl cellulose.

The compounds of this invention are very effective stabilizers for a host of organic substrates subject to light induced deterioration and are expected to be resistance to loss from a stabilized composition during high temperature.

Thus, the compounds of this invention are particularly useful as stabilizers for the protection of polyesters, for instance poly(ethylene terephthalate), poly(butylene terephthalate) or copolymers thereof; of polycarbonates, for example polycarbonate derived from bisphenol A and phosgene, or copolymers thereof; of polysulfones; of polyamides such as NYLON-6, NYLON-6,6, NYLON 6,10 and the like as well as copolyamides; of thermoset acrylic resins; of thermoplastic acrylic resins; of polyolefins such as polyethylene, polypropylene, copolyolefins and the like; and of any polymer system requiring high temperature processing and fabrication.

In general, the UV stabilizers of this invention are employed at from about 0.1 to about 5% by weight of the stabilized composition, although this will vary with the particular substrate and application although a higher level can also be used. An advantageous range is from about 0.5 to about 3%.

The UV absorbing compounds (also designated as "light stabilizers" or simply "stabilizer") of Formula I may readily be incorporated into the organic polymers by conventional techniques, at any convenient stage prior to the manufacture of shaped articles or coatings therefrom. For example, the stabilizer may be mixed with the polymer in dry powder form, or a suspension or emulsion of the stabilizer may be mixed with a solution, suspension, or emulsion of the polymer.

Fabricated polymer compositions, e.g., plastic parts or objects may be formed by heating the polymer to its softening point in an extruder and adding the UV absorbing compound and other additives to the melt to form a substantially uniform physical mixture.

Thermoplastic polymer materials susceptible to UV damage and the compounds of the invention can be blended in the desired quantities and heated to a temperature above the softening point of the polymer. The heating in an extruder and blending of the coupled compound are done as known in the art. The heating and blending can be done in either order, however, in the preferred embodiment, these processes are conducted simultaneously. The mixing may be conducted in any suitable equipment including a Banbury mixer, single or twin screw extruder, ribbon blender, injection molding machine, two-roll mill or the like, thus forming a substantially uniform blend of the polymer material and the coupled compound. The mixing step is usually conducted for from about 0.1 minutes to about 20 minutes, preferably to about 10 minutes, at a temperature ranging from about 38° C. to about 350° C.

The UV absorbing materials of the invention are useful in stabilizing thermosetting and thermoplastic acrylic resins, thermocrosslinkable acrylic, alkyd or polyester resins which are used for automobile finishes and similar coating applications. These substances are described in "Encyclopedia of Polymer Science and Technology", Interscience Publishers, New York, Volume 1 (1964), on pages 273 to 276 and Volume 13 (1970), on pages 530 to 532, and also in "Understanding Paint" by W. R. Fuller in American Paint Journal, St. Louis, 1965, pages 124 to 135.

Acrylic, alkyd or polyester resins and resin lacquers which can be stabilized in accordance with the invention against the action of light, oxygen and moisture are the customary stoving lacquers, for example those described in H. Kittel's "Lehrbuch der Lacke and Beschichtungen" ("Textbook of Lacquers and Coatings"), Volume 1, Part 2, pages 735 and 742 (Berlin, 1972), and in H. Wagner, H. F. Sarx, "Lackkunstharze" ("Synthetic Resins for Lacquers"), pages 229 to 235.

The stabilization, by means of the compounds according to the invention, of metal effect lacquers based on an acrylic resin which can be crosslinked by heat is another relevant application. An unstabilized metal effect lacquer prepared from these resins is unsuitable, in spite of its excellent physical and chemical properties, since the UV light can pass unhindered through the top coat and leads to cracking in the coat below. Other lacquers and coatings which can be crosslinked by heat and are based on acrylic resins, melamine resins, alkyd resins, polyester resins, epoxy resins or mixtures thereof, can also be stabilized effectively by means of the compounds according to the invention.

In order to achieve the metal effect, the conventional aluminum pigments are used in a concentration of 1 to 10% by weight, relative to solvent-free binder (lacquer resin). The stabilized lacquers can be applied by the conventional one-coat or two-coat processes. In the latter case the initial lacquer containing the pigment is first applied and is then overlaid with transparent lacquer. The lacquer preferably contains 0.5 to 5% of the UV absorbing compounds of the invention.

Further additives which can be present in the lacquer are other customary light stabilizers, phenolic antioxidants, pigments, dyes, metal deactivators and the like.

The UV absorbing compounds are useful in stabilizing stoving lacquers especially two-layer uni-lacquer coatings based on thermocrosslinkable acrylic, alkyd or polyester resins, which if desired can be crosslinked with melamine/formaldehyde resins, epoxide resins or polyisocyanates against the action of light. The lacquers are typically applied by the conventional two coat process, for example by spraying the undercoat lacquer containing a pigment in a layer thickness of 20-30μ onto coil-coated sheet metal, onto which a commercially available filler had previously been baked in a layer thickness of 20-30μ, and, after air-drying for about 5 minutes, applying the topcoat lacquer wet-in-wet in a layer thickness of 35-40μ. After further air-drying for about 15 minutes, the lacquer is baked at 80° C.-150° C., depending on the nature of the crosslinking agent, for about 30 minutes.

The UV absorbing compounds and any additional additives used for stabilization according to the invention can be incorporated either only into the unpigmented topcoat lacquer or both into the unpigmented topcoat lacquer and into the undercoat lacquer containing pigment. Preferably, the light stabilizer is incorporated in the unpigmented topcoat lacquer such as topcoat lacquers based on acrylic/melamine resins.

The invention also relates further to stabilized organic material which is in the form of photographic material or is part of a photographic material, the photographic material containing, preferably in top layers, 0.1 to 5% by weight, relative to the photographic material without stabilizer, of the UV absorbing compounds according to the invention.

Although the compounds of the invention may be used above to provide a light stabilizing function, the compounds of this invention are often combined with other stabilizers, even other light stabilizers, in the preparation of stabilized compositions. The stabilizers may be used with phenolic antioxidants, pigments, colorants or dyes, light stabilizers such as hindered amines, metal deactivators, etc.

Examples of suitable materials that can be incorporated as optional ingredients, typically at levels from about 0.1 to about 10%, preferably from about 0.5 to about 5% by weight include the following additives.

Antioxidants such as various phenols, derivatives of hydroquinones, hydroxylated thiodiphenyl ethers; alkylidenebisphenols; O-, N- and S-benzyl compounds; Hydroxybenzylated malonates; hydroxybenzyl-aromatic compounds; s-triazine compounds; amides of β-(3,5-di-tert.-butyl-4-hydroxyphenyl)-propionic acid; esters of β-(3,5-di-tert-butyl-4-hydroxyphenyl)-propionic acid with monohydric or polyhydric alcohols; esters of .beta.-(5-tert.-butyl-4-hydroxy-3-methylphenylpropionic acid with monohydric or polyhydric alcohols, such as for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thiapentadecanol, trimethylhexanediol, trimethylolethane, trimethylolpropane, tri-hydroxyethyl isocyanurate and 4-hydroxymethyl-1-phospha-2,6,7-trioxabicyclo[2.2.2]octane; esters of 3,5-di-tert-butyl-4-hydroxyphenylacetic acid with monohydric or polyhydric alcohols; benzylphosphonates, and suitable mixtures thereof.

Light-stabilizers such as esters of optionally substituted benzoic acids; sterically hindered amines or amino ethers such as are described in U.S. Pat. No. 4,547,537 to Ackerman et al incorporated by reference herein, for example; bis(1-octyloxy-2,2,6,-tetramethyl-4-piperidyl)sebacate, 4-benzoyl-2,2,6,6-tetramethylpiperidine, 4-stearyloxy-2,2,6,6-tetramethylpiperidine, bis-(2,2,6,6-tetramethylpiperidyl) sebacate, bis-(1,2,2,6,6-pentamethylpiperidyl)2-n-butyl-2-(2-hydroxy-3,5-di-tert-butylbenzyl)malonate or 3-n-octyl-7,7,9,9-trimethyl-1,3,8-triazaspiro[4.5]decane-2,4-dione; oxalic acid diamides; metal deactivators such as oxanilide, isophthalic acid dihydrazide; basic co-stabilizers; nucleation agents, e.g., 4-tert.-butylbenzoic acid, adipic acid or diphenylacetic acid; phosphites and phosphonites and suitable mixtures thereof.

Examples of other suitable sterically hindered amines are amines such as are described in German Offenlegungsschrift 2,500,134, in U.S. Pat. No. 4,110,304 or in the "Taschenbuch der Kunststoff-Additive" ("Pocketbook of Plastics Additives") by R. Gachter and H. Muller (Hanser Verlag, Munich, 1979), Bis-(1,2,2,6,6-pentamethyl-4-piperidyl)sebacate or bis-(1,2,2,6,6-pentamethyl-4-piperidyl)2-n-butyl-2-(3,5-di-tert.-butyl-4-hydroxybenzyl)malonate.

Useful sterically hindered amines are those based on 2,2,6,6-tetraalkylpiperidine as described is U.S. Pat. No. 4,314,933 to Berner et al incorporated by reference herein.

Another class of suitable light stabilizers are the so-called N—OR$_1$—substituted hindered amines disclosed in U.S. Pat. No. 5,112,890 to Behrens et al incorporated by reference herein. Examples of these hindered ether amine stabilizers include: (1-acetoxy-2,2,6,6-tetramethylpiperidin-4-yl)-4-hydroxy-3,5-di-tert-butylbenzoate; di-(12-acetoxy-2,2,6,6-tetramethylpiperidin-4-yl)sebacate; 2-(4-hydroxy-3,5-di-tert.butylbenzyl)-2-(1-acetoxy-2,2,6,6-tetramethylpiperdin-4-yl)n-butylmalonate; di-(1-cyclohexyloxy-2,2,6,6-tetramethylpiperidin-4-yl)sebacate; di-(1-heptyloxy-2,2,6,6-tetramethylpiperdin-4-yl)sebacate; di-(1-methoxy-2,2,6,6-tetramethylpiperdin-4-yl)sebacate; di-(1-nonyloxy-2,2,6,6-tetramethylpiperdin-4-yl)sebacate; di-[1-(alpha-methylbenzyloxy)-2,2,6,6-tetramethylpiperdin-4-yl) sebacate; di-(1-benzoyloxy-2,2,6,6-tetramethylpiperdin-4-yl)sebacate; di-(1-benzyloxy-2,2,6,6-tetramethylpiperdin-4-yl)sebacate; di-[1-(alpha-methylbenzyloxy)-2,2,6,6-tetramethylpiperidin-4-yl]terephthalate; di-(1-n-butylcarbamoyloxy-2,2,6,6-tetramethylpiperidin-4-yl)n-butylamalonate; di-(1-ethoxy-2,2,6,6-tetramethylpiperdin-4-yl)sebacate; and di-(1-octyloxy-2,2,6,6-tetramethylpiperdin-4-yl)sebacate.

Other additives that can be incorporated in the stabilized compositions are thiosynergists such as dilauryl thiodipropionate, lubricants such as stearyl alcohol, fillers and reinforcing agents, asbestos, kaolin, talc, glass fibers, pigments, optical brighteners, flameproofing agents and antistatic agents, blowing agents, calcium carbonates, silicates, barium sulfate, metal oxides and hydroxides, carbon black and graphite.

Sterically hindered amine light stabilizers are especially useful in combination with the UV absorbing compounds of the invention to provide additional protection in coatings especially against light, water and humidity. The combination of sterically hindered amines and the stabilizers according to the invention makes possible excellent retention of gloss when exposed to weathering as well as resistance to blistering and flaking in stoving lacquer coatings such as are used for application of automobile top lacquers and acid catalyzed thermoset resin coating compositions to improve resistance against the deleterious effects of light, moisture and oxygen without inhibition of curing time.

The light stabilizing compounds of the invention can also be used in combination with other classes of UV absorbing compounds such as benzophenones, benzotriazoles, acrylic acid derivative, aryl-s-triazines, organic nickel compounds and oxanilides.

Non-limiting examples of suitable benzotriazole UV absorbing compounds which can be used in combination with the UV absorbing compounds of the invention include: 2-[2-hydroxy-3,5-di(alpha,alpha-dimethyl-benzyl)phenyl]-2H-benzotriazole, 2-(2-hydroxy-3,5-di-tert-octylphenyl)-2H-benzotriazole, 2-(2-hydroxy-3-alpha,alpha-dimethylbenzyl-5-tert-octylphenyl)-2H-benzotriazole, 2-(2-hydroxy-3-tertoctyl-5-alpha,alpha-dimethylbenzylphenyl)-2H-benzotriazole, 2-[2-hydroxy-3-tert-butyl-5-(2(omega-hydroxy-octa(ethyleneoxy)carbonyl)ethylphenyl]-2H-benzotriazole, 2-(2-hydroxy-3,5-di-tert-amylphenyl)-2H-benzotriazole, dodecylated 2-(2-hydroxy-5-methylphenyl)-2H-benzotriazoles, 5-chloro-2-[2-hydroxy-3,5-di(alpha,alpha-dimethylbenzyl)-phenyl]-2H-benzotriazole, 5-chloro-2-(2-hydroxy-3-alpha,alpha-dimethylbenzyl-5-tert-octylphenyl)-2H-benzotriazole, 5-chloro-2-(2-hydroxy-3-tert-octyl-5-alpha,alpha-dimethylbenzylphenyl)-2H-benzotriazole, 5-chloro-2-[2-hydroxy-3-tertbutyl-5-(2-(omega-hydroxyocta-(ethyleneoxy)-ethylphenyl]-2H-benzotriazole, 5-chloro-2-(2-hydroxy-5-tert-octylphenyl)-2H-benzotriazole, 5-chloro-2-(2-hydroxy-3,5-diatert-amylphenyl)-2H-benzotriazole, and 5-chloro-2-[2-hydroxy-3-tert.butyl-5-(2-octyloxycarbonyl)ethylphenyl]-2H-benzotriazole.

EXAMPLES

The following examples are shown as illustrations of the invention and are not intended in any way to limit its scope.

Example 1

Preparation of 2-(2-Hydroxy-3-Benzoyl-5-Methyl-Phenyl)Benzotriazole 112.5 g 2-(2-hydroxy-5-methyl phenyl)benzotriazole, 84 g benzoyl chloride and 133 g aluminum chloride were dissolved in 1000 ml $CH_2Cl_2$. The mixture was refluxed for 2 hours before $CH_2Cl_2$ was removed completely from the mixture via distillation to obtain an ester intermediate in the 3-neck round bottom flask. The temperature was then raised to 160° C. and the mixture in the molten state was mixed thoroughly with a mechanical agitator for 30 minutes. The heating was then stopped and the mixture was stirred until the temperature dropped to bellow 90° C. At this point, enough water was added into the mixture until no more bubbles from the decomposition of aluminum chloride was detected.

500 ml of additional water was then added to the mixture along with 50 g of concentrated HCl. The mixture was then stirred under reflux conditions for another hour before cooling to room temperature. The aqueous layer was then discharged completely and 500 ml water was added to the mixture along with 50 g of 45% NaOH. The mixture was then refluxed for another hour before cooling to room temperature. The aqueous layer was again discharged. 500 ml of water is then added along with another 50 g of concentrated HCl, mixed under reflux, cooled and the aqueous phase separated. The remaining organic phase was then washed with water several times and dried to obtain a solid with a melting point of 166 to 167.8° C. (compound 1). The yield was 65% (107 grams).

A sample of the product was dissolved in methylene chloride and analyzed by GC. A single peak was obtained whose retention time was different and longer than either of the starting reactants and ester intermediate.

The $^1$H NMR peak assignments confirm the presence of the 2-hydroxy group and the ortho benzoyl group consistent with compound 1 being 2-(2-hydroxy-3-benzoyl-5-methyl-phenyl)benzotriazole.

The ester intermediate was also obtained via a typical esterification of benzoic acid and 2-(2-hydroxy-5-methyl-phenyl)benzotriazole under strong acidic conditions such as sulfuric acid or p-toluene sulfonic acid. The UV spectra of ester intermediate isolated prior to the Fries Rearrangement and the one obtained from the above esterification process are identical and is given in FIG. 1 as curve D. Evidently, curve D exhibits no typical benzotriazole UV absorption as well as no typical benzophenone UV absorption. This confirmed the product, 2-(2-hydroxy-3-benzoyl-5-methyl-phenyl)benzotriazole, was not an ester.

Further confirmation that the product was 2-(2-hydroxy-3-benzoyl-5-methyl-phenyl)benzotriazole was provided by the UV spectrum given in FIG. 1. Curve A is the spectrum of the product. Curve B is the spectrum of 2-(2-hydroxy-3-cumyl-5-tert.Octyl-phenyl)benzotriazole a typical benzotriazole UV absorber of the prior art. Curve C is the spectrum of 2-hydroxy-4-methyl benzophenone. Two features are observed on comparing curves A and B. First, in curve the two peaks present in the spectrum of the typical benzotriazole (curve B) present at about 310 and 350 nm are of comparable intensity. In contrast, the spectrum of product, 2-(2-hydroxy-3-benzoyl-5-methyl-phenyl)benzotriazole (curve A), exhibits a relatively stronger absorption at 350 nm as well as greater absorption at wavelengths below 300 nm. These spectral features of the product are consistent with a structure which contains both 2-hydroxy phenyl benzotriazole (curve B) and benzophenone chromophores (curve C).

The evidence provides by GC, $^1$H NMR, and UV spectroscopy and the isolation of ester intermediate demonstrate that compound 1 is 2-(2-hydroxy-3-benzoyl-5-methyl-phenyl)benzotriazole.

Example 2

Preparation of 2-(2-hydroxy-3-benzoyl-5-tert.Butyl-phenyl)benzotriazole 2-(2-hydroxy-3-benzoyl-5-tert.-butyl-phenyl)benzotriazole would be anticipated to be made by the following process. 130.2 g 2-(2-hydroxy-5-t-butyl-phenyl)benzotriazole, 84 g benzoyl chloride and 133 g aluminum chloride are dissolved in 1000 ml $CH_2Cl_2$. The mixture is refluxed for 2 hours before $CH_2Cl_2$ is removed completely from the mixture via distillation. The temperature is then raised to 160° C. and the mixture in molten state is mixed thoroughly with a mechanical agitator for 30 minutes. The heating is then stopped and the mixture is stirred until the temperature dropped to bellow 90° C. At this point, enough water is added into the mixture until no more bubbles from the decomposition of aluminum chloride is detected.

500 ml of additional water is then added to the mixture along with 50 g of concentrated HCl. The mixture is then stirred under reflux conditions for another hour before cooling to room temperature. The aqueous layer is then discharged completely and 500 ml water is added to the mixture along with 50 g of 45% NaOH. The mixture is then refluxed for another hour before cooling to room temperature. The aqueous layer is again discharged. 500 ml of water is then added along with another 50 g of concentrated HCl, mixed under reflux, cooled and the aqueous phase separated. The remaining organic phase is then washed with water several times and dried to obtain the 2-(2-hydroxy-3-benzoyl-5-methyl-phenyl)benzotriazole (compound 2) whose structure would be confirmed by the methods set forth in Example 1.

Example 3

Preparation of 2-(2-hydroxy-3-(m-methyl benzoyl)-5-methyl-phenyl)benzotriazole 2-(2-hydroxy-3-(m-methyl benzoyl)-5-methyl-phenyl)benzotriazole would be anticipated to be made by the following process. 112.5 g 2-(2-hydroxy-5-methyl-phenyl)benzotriazole, 92.8 g m-methyl benzoyl chloride and 133 g aluminum chloride are dissolved in 1000 ml $CH_2Cl_2$. The mixture is refluxed for 2 hours before $CH_2Cl_2$ is removed completely from the mixture via distillation. The temperature is then raised to 160° C. and the mixture in molten state is mixed thoroughly with a mechanical agitator for 30 minutes. The heating is then stopped and the mixture is stirred until the temperature dropped to bellow 90° C. At this point, enough water is added into the mixture until no more bubbles from the decomposition of aluminum chloride is detected.

500 ml of additional water is then added to the mixture along with 50 g of concentrated HCl. The mixture is then stirred under reflux conditions for another hour before cooling to room temperature. The aqueous layer is then discharged completely and 500 ml water is added to the mixture along with 50 g of 45% NaOH. The mixture is then refluxed for another hour before cooling to room temperature. The aqueous layer is again discharged. 500 ml of water is then added along with another 50 g of concentrated HCl, mixed under reflux, cooled and the aqueous phase separated. The remaining organic phase is then washed with water several times and dried to obtain the 2-(2-hydroxy-3-benzoyl-5-methyl-phenyl)benzotriazole (compound 3) whose structure would be confirmed by the methods set forth in Example 1.

Example 4

Preparation of 2-(2-Hydroxy-3-Acetyl-5-Methyl-Phenyl)Benzotriazole 45 g 2-(2'-hydroxy-5'-methyl-phenyl)benzotriazole, 16 g acetyl chloride and 60 g aluminum chloride were dissolved in 200 ml CH2Cl2. The mixture was refluxed for 2 hours before $CH_2Cl_2$ was removed completely from the mixture via distillation. Then temperature was raised to 130° C. while the mixture in molten state was mixed thoroughly with a mechanical agitator for 60 minutes; then stopped heating and agitation all together until temperature dropped to bellow 100° C. At this point, enough water was added into the mixture until generated no more bubbles.

Additional 200 ml water was added into the mixture with 50 g conc. HCl; then refluxed for another hour before the mixture was cooled down to room temperature. After the aqueous layer was discharged completely the product was washed with 200 ml water twice. Then 600 ml of water with 50 g 10% NaOH was added and refluxed for another hour before the mixture was cooled down and aqueous layer was discharged again. Finally, the product was washed with 100 ml water twice then dried to obtain 32 g 2-(2'-hydroxy-3'-acetyl-5'-methyl-phenyl)benzotriazole, designated Compound 4 whose structure was confirmed by the methods employed in Example 1. The absorption spectra of Compound 4 is shown a FIG. 2, curve E. The characteristic spectral features are clearly evident (double peaks indicating the presence of the 2-hydroxy group, and the high UV absorption at low wavelengths characteristic of the 3-keto group)

Example 5

Preparation of 2-(2-Hydroxy-3-Nonanoyl-5'-Methyl-Phenyl)Benzotriazole

Similar to the above example 4, 16 g acetyl chloride was replaced with 40 g of nonanoyl chloride in the reactions. Since the alkyl chain was fragmented under Fries Rearrangement at high temperature, the final product was composed of a statistical mixtures of different chain lengths of alkyl groups as evidenced by multiple GC peaks having retention times in the range of different molecular weight ketones. The total weight of the mixture was 45.3 g. The product, designated as compound 5, was a liquid which is consistent with the presence of different isomers that interfere with crystallization as discussed above. The absorption spectra of Compound 5 is shown a FIG. 2, curve F. The characteristic spectral features are again clearly evident.

Figure 2:
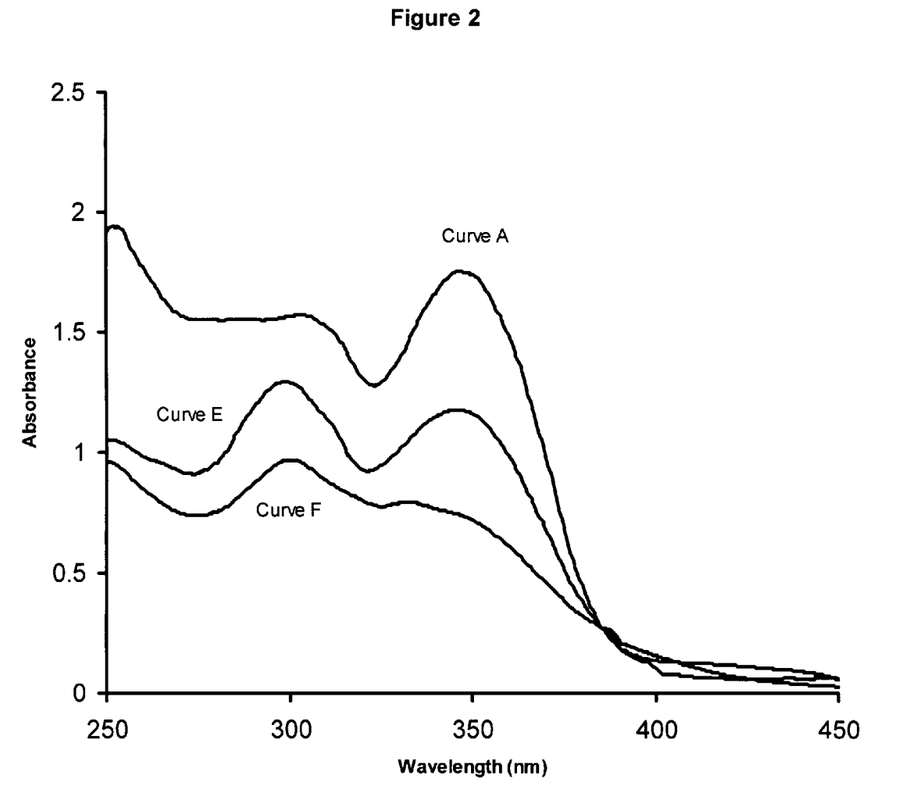

FIG. 2 illustrates that the characteristics of UV absorption spectra of ketone derivatives of 2-(2-hydroxyphenol)benzotriazole are the same regardless whether $R^2$ is aliphatic or aromatic moiety in formula I. The results also illustrate the additional UV absorption of the benzophenone-benzotriazole hydrid structure discussed above (compare curves E and F with Curve A).

Example 6

Extinction Coefficient of 2-(2-hydroxy-3-benzoyl-5-methyl-phenyl)benzotriazole Compared with Benzotriazoles of the Prior Art 0.2185 gm compound 1 (2-(2-hydroxy-3-benzoyl-5-methyl-phenyl)benzotriazole) was dissolved in 100 ml $CHCl_3$ to prepare a stock solution. 1.5 ml of stock solution was diluted in $CHCl_3$ to 100 ml to a final concentration of $2.19 \times 10^{-5}$ gram/ml and an alequate was transferred to a 1 cm path-length quartz cuvette. A UV spectrum was acquired and the absorption peak(s) were determined.

The UV spectrum of a commercially available UV absorbing benzotriazole derivative, TINUVIN 928 (2-(2-hydroxy-3-cumyl-5-tert.Octyl-phenyl)benzotriazole) in $CHCl_3$ was obtained in an analogous manner.

Extinction coefficients of each of the above compounds at their absorption maxima were derived from Bear's Law, (i.e., Absorbance equals extinction coefficient times path-length times concentration (wt % or molarity). The results are collected in Table 1 below and indicate that the mass extinction coefficient of the UV absorbing compound of the invention by virtue of its benzotriazole-benzophenone hybrid structure is about 35% higher than a typical benzotriazole of the prior art.

TABLE 1

| Compositions and properties of | | |
|---|---|---|
| Sample | Relative Molar Extinction Coefficient | Relative Extinction Coefficient by Weight |
| Control Tinuvin 928 @ 350 nm | 1 | 1 |
| Compound 1 @ 345 nm | 1.13 | 1.52 |

Example 7

Influence of Benzotriazole Stabilizers on Retention of Gloss Values of Thermoset Acrylic Coatings after Accelerated Weathering.

The influence of the hybrid benzotriazole compounds 1-3 as prepared in the above examples on gloss retention of thermoset acrylic coatings can be demonstrated by the following procedure. Several thermoset acrylic resins and an alkyd/acrylic resin systems can be formulated with 2% by weight of benzotriazole light absorber stabilizers of the invention and cast onto glass plates as 1μ thick coatings. The coatings can be cured by heating at elevated temperatures for selected periods of time, e.g., 120° C. to 150° C. for 20 to 30 minutes. The loss of benzotriazole light stabilizer during coating/curing can be ascertained by UV-absorption analysis of the coatings. Any decrease in absorbance of the coatings can be correlated to loss of benzotriazole stabilizer during the curing step.

These cured coatings can then be subjected to the accelerated weathering test involving alternating 4-hour periods of UV irradiation at 60° C. with a 4-hour period of condensation (rain) at 50° C. for each cycle for a total of 670 hours. Again any decrease in absorbance of the weathered coatings can be correlated to loss of the benzotriazole stabilizer during the curing and weathering period.

Formulations containing Compounds 1 are expected to consistently provide much higher retention of gloss values after accelerated weathering relative to a control have no light absorbers.

Example 8

Influence of Benzotriazole Stabilizers on Retention of Gloss Values of Acrylic Enamels and Lacquers after Accelerated Weathering The influence of the hybrid benzotriazole compounds 1 as prepared in the above examples on gloss retention can be demonstrated by the following procedure. Samples of several thermoset acrylic enamels and a thermoplastic acrylic lacquer can be formulated to include the UV light stabilizer.

Gloss values can be compared for the initial enamel or lacquer and after exposure to a multi-cycle accelerated weathering test where each cycle includes 4 hours of UV exposure at 60° C. and 4 hours of condensation (moisture) at 50° C.

Formulations containing Compound 1 at a level of incorporation in the test pieces of 1% and 2% by weight are expected to give consistently much higher gloss values after 200 cycles (800 hours) and 50 cycles (200 hours) of accelerated weathering relative to a control have no light absorbers.

Example 9

Stabilization of Polyethylene Terephthalate

The stabilization of polyethylene terephthalate can be demonstrated by the following procedure. 0.5% of the compound 1 of Example 1 can be added as a stabilizer to molten polyethylene terephthalate at 270° C. with stirring under a nitrogen atmosphere. The resulting formulated polymer can then be ground with solid carbon dioxide.

The stabilized composition can then be extruded at elevated temperature into a film with little loss of stabilizer expected. The film is then exposed to actinic radiation. The stabilized film is expected to retain desirable physical properties for a longer period than does a film prepared from unstabilized polyester.

Example 10

Stabilization of Polycarbonate

The Stabilization of Polycarbonate by the UV absorbing compounds of the invention can be demonstrated by the following procedure. Polycarbonate (Lexan, General Electric) is mixed in a compounding extruder with, for example, 0.3% of either of the compounds prepared in Example 1. The stabilized composition can be extruded into a sheet at elevated temperature with little loss of stabilizer. The sheet is anticipated to maintain its physical properties after exposure to UV light for a longer period of time than does a sheet containing no stabilizer.

Example 11

Gloss and Delamination Values of Topcoats of Thermoplastic Acrylic Lacquer

The influence of the UV absorbing compounds of the invention alone or in combination with sterically hindered amine light stabilizers can be demonstrated by the following procedure. Silver metallic thermoplastic acrylic lacquer can be formulated to include for example compound 1, compound 2 or compound 3, alone or in combination with either bis(2,2,6,6-tetramethyl-4-piperidyl)sebacate or bis(1,2,2,6,6-pentamethyl-4-piperidyl)2-n-butyl-2-(3,5-di-tert-butyl-4-hydroxybenzyl)malonate; (1-acetoxy-2,2,6,6-tetramethylpiperidin-4-yl)-4-hydroxy-3,5-di-tert-butylbenzoate; di-(12-acetoxy-2,2,6,6-tetramethylpiperidin-4-yl)sebacate; 2-(4-hydroxy-3,5-di-tert.butylbenzyl)-2-(1-acetoxy-2,2,6,6-tetramethylpiperdin-4-yl)n-butylmalonate. The lacquer can then be sprayed as a topcoat over a primer surface consisting of an epoxy ester on a metallic panel. The cure schedule is heating for 10 minutes at 48° C. and then for 30 minutes at 155° C. The initial topcoat film thickness is 2.0 to 2.2 mils (50 to 55 microns, 0.0508 to 0.0559 mm).

The panels can then be exposed for one year in the climate such as South Florida or Porto Rico in an unheated black box at an angle of 5° to the sun.

The panels following the prolonged exposure are then conditioned for 96 hours in a constant humidity chamber at 38° C. and 100% relative humidity. The panels are then removed from the chamber, wiped dry and immediately evaluated using a cross-hatch tape adhesion test. The panels are then allowed to recover for one hour at room temperature before the cross-hatch tape adhesion test is run at a different spot on the same panel. Samples generally show some improved delamination resistance following the one hour recovery period from the most severe delamination condition namely immediately after humidification.

The cross-hatch tape adhesion test involves using a multi-cut knife to prepare cross-hatches through the topcoat film on the panel. A acetate fiber adhesive tape is placed over the cross-hatch area and then is pulled off. A visual inspection of the amount of topcoat, if any, coming off with the tape as it is pulled gives a relative rating of the amount of delamination. A rating system of 0 meaning no cross-hatch delamination to 5 meaning complete cross-hatch delamination can be employed.

The results of the above treatments are expected to demonstrate that samples containing the UV absorbing compounds 1 of the instant invention exhibit excellent resistant to loss of gloss during prolonged sun exposure compared with a control containing no stabilizer and that films containing both the UV absorbing compounds in combination with the piperidyl containing hindered amines exhibit the greatest resistance to delamination after prolonged sun exposure.

The results are further expected to show that compound 1 protect a thermoplastic acrylic topcoat from delamination after one year of intense sun exposure under the most severe testing conditions immediately following humidification.

Example 12

The following example illustrates how the improvement in color protection of pigmented compositions provided by the UV absorbing compounds of the invention can be determined.

The UV absorbing compound 1 is dry blended with polyacetal pellets (DELRIN.R™ 500P NC010, DuPont) using a mixer. The dry blend is extruded and pelletized using a twin screw extruder at a melt temperature of about 210° C. The pellets are molded into test plaques using an injection molder operated at about 210° C. The plaques are exposed in a Xenon-arc Weather-Ometer according to automotive test procedure SAE J1885. Exposure is measured in terms of the total irradiation, measured in kilojoules per square meter ($kJ/m^2$). Color change in the exposed samples is determined by measuring the color of the exposed samples compared to the unexposed samples as color difference ($\Delta E$) according to ASTM D2244.

Incorporation of compound 1 is anticipated to significantly reduce the change in color, i.e., color difference between the exposed and non-exposed samples relative to a control which does not contain the UV absorbing compounds.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

What is claimed is:

1. A composition of matter comprising:
   i) a polymer selected from the group consisting of polyesters, polycarbonates, polyester resins, polysulfones, polyamides, acrylic polymers, acrylic resins, alkyd resins, polyolefins, polystyrenes, vinyl polymers, polyvinylchloride, polyureas, polyurethanes, poly hydrocarbons, polypeptides, cellulose polymers, cellulose ethers, cellulose esters, latex polymers, and combinations thereof;
   ii) from 0.01 to 10% of an ultraviolet light absorbing compound or compounds having the formula I that acts as stabilizer against damage from UV radiation:

wherein
$R^1$ is is selected from the group consisting of hydrogen, a halogen atom, a straight-chain or branched lower alkyl or lower alkoxy of 1 to 4 carbon atoms;
$R^2$ is selected from the group consisting of, a propyl group, a butyl group, an amyl group, a hexyl group, an octyl group, a nonyl group, an isopropyl group, a tertiary butyl group, a tertiary octyl group, a 2-ethylhexyl group, a cumyl group, a cyclohexyl group, a cyclohexyl group substituted with an alkyl group of 1 to 4 carbon atoms and a cyclohexyl group substituted with an alkoxyl group of 1 to 4 carbon atoms; and
R3 is selected from the group consisting of a straight-chain or branched alkyl of 1 to 14 carbon atoms, an alkylaryl group of 7 to 12 carbon atoms, an alkoxy group of 1 to 4 carbon atoms, a phenyl group, a phenyl group substituted with an alkyl group of 1 to 8 carbon atoms, a cycloalkyl group of 5 to 6 carbon atoms, a carboalkoxy group of 2 to 9 carbon atoms, chlorine, and an arylalkyl group of 7 to 9 carbon atoms; and wherein the ultraviolet light absorbing compound or compounds is prepared by a process comprising the steps of:
   (a) reacting a 2-benzotriazolyl-4-hydrocarbyl phenol with an acid chloride or an organic acid or an organic anhydride in the presence of an acid catalyst and an optional solvent at a temperature up to reflux conditions wherein the ratio the 2-benzotriazolyl-4-hydrocarbyl phenol to the acid chloride, organic acid or organic anhydride is about 3:1 to about 1:3;
   (b) increasing the temperature to between about 100° C. and about 200° C. for a period of time sufficient to produce the UV absorbing compound of Formula I by a Fries rearrangement.

2. The composition of matter according to claim 1, wherein $R^2$ is selected from the group consisting of an isopropyl group, a tertiary butyl group, a tertiary octyl group, a 2 ethylhexyl group, a cumyl group, a cyclohexyl group, a cyclohexyl group substituted with an alkyl group of 1 to 4 carbon atoms and a cyclohexyl group substituted with an alkoxyl group of 1 to 4 carbon atoms.

3. The composition of matter according to claim 1, wherein $R^2$ is selected from the group consisting of a cyclohexyl group, a cyclohexyl group substituted with an alkyl group of 1 to 4 carbon atomsand a cyclohexyl group substituted with an alkoxyl group of 1 to 4 carbon atoms.

4. The composition of matter according to claim 1, wherein $R^2$ is selected from the group consisting of an isopropyl group, a tert. butyl group, a tert.octyl group, a 2-ethyl hexyl group, and a cumyl group.

5. The composition of matter according to claim 1, wherein the polymer is film forming.

6. The composition of matter according to claim 1, wherein the composition further comprises a dye or a pigment, or metal particles.

7. The composition of matter according to claim 1, further comprising at least one sterically hindered amine stabilizer selected from the group consisting of polyalkylpiperidines, N—OR substituted hindered amines and a combination thereof.

8. The composition of matter according to claim 1, wherein the composition of matter is a thermoplastic or thermosetting polymer.

9. The composition of matter according to claim 1 wherein the acid chloride is selected from the group consisting of an unsubstituted or substituted alkanoyl chloride, an unsubstituted or substituted cylclohexanoyl chloride.

10. The composition of matter according to claim 1 wherein the optional solvent is an aprotic solvent selected from the group consisting of methylene chloride, toluene, benzene, xylene, hexane, heptane, petroleum ethers, mineral spirits, furan, tetrahydrofuran, dioxane, dimethylsulfoxide, ethylene glycol monoacetate, ethylene glycol diacetate, diethylene glycol monobutyl ether and mixtures thereof.

11. The composition of matter according to claim 1 wherein the process further comprises purification of the product formed in step (b) by successive extractions in which esters that may be present in the product mixture are hydrolyzed, converted to water soluble variants by hydrolysis and extracted into an aqueous phase.

12. The composition of matter according to claim 1 wherein the composition comprises a mixtures of the UV absorbing compounds having Formula I in which the individual components of the mixture differ in one or more of the $R^1$, $R^2$ or $R^3$ substituent groups, and wherein the mixture is formed by employing a mixture of different 2-benzotriazolyl-4-hydrocarbyl phenols and/or acid chloride reactants in process step (a).

* * * * *